United States Patent
Kim et al.

(10) Patent No.: US 10,927,131 B2
(45) Date of Patent: *Feb. 23, 2021

(54) NEAR-INFRARED ABSORBING COMPOSITION, OPTICAL STRUCTURE, AND CAMERA MODULE AND ELECTRONIC DEVICE COMPRISING THE SAME

(71) Applicant: Samsung Electronics Co., Ltd., Suwon-si (KR)

(72) Inventors: Mi Jeong Kim, Hwaseong-si (KR); Myungsup Jung, Seongnam-si (KR); Jong Hoon Won, Yongin-si (KR); Changki Kim, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/522,256

(22) Filed: Jul. 25, 2019

(65) Prior Publication Data

US 2020/0031849 A1    Jan. 30, 2020

(30) Foreign Application Priority Data

Jul. 26, 2018 (KR) .......................... 10-2018-0087193

(51) Int. Cl.
*C07F 1/00* (2006.01)
*G02B 5/22* (2006.01)
(Continued)

(52) U.S. Cl.
CPC ............ *C07F 1/005* (2013.01); *C07C 309/04* (2013.01); *C07C 309/30* (2013.01); *C07F 9/09* (2013.01);
(Continued)

(58) Field of Classification Search
CPC .......... C07F 1/005; C07F 9/09; C07C 309/04; C07C 309/30; G02B 5/223; G02B 13/0025; G02B 27/1013
See application file for complete search history.

(56) References Cited

U.S. PATENT DOCUMENTS 6,592,784 B2    7/2003   Hasegawa et al.
8,349,467 B2    1/2013   Naoi
                (Continued)

FOREIGN PATENT DOCUMENTS

CN    101070330 A    11/2007
JP     3135332 B2     2/2001
              (Continued)

*Primary Examiner* — Bijan Ahvazi
(74) *Attorney, Agent, or Firm* — Harness, Dickey & Pierce, P.L.C.

(57) ABSTRACT

Disclosed are a near-infrared absorbing composition including a copper complex represented by Chemical Formula 1, a near-infrared absorption layer formed by using the near-infrared absorbing composition including the copper complex represented by Chemical Formula 1, an optical structure including the near-infrared absorption layer, and a camera module or an electronic device including the optical structure, wherein Chemical Formula 1 is provided below, and

[Chemical Formula 1]

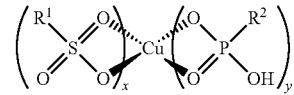

and in Chemical Formula 1, $R^1$, $R^2$, x, and y are the same as described in the detailed description.

22 Claims, 8 Drawing Sheets

(51) Int. Cl.
*G02B 13/00* (2006.01)
*G02B 27/10* (2006.01)
*C07F 9/09* (2006.01)
*C07C 309/04* (2006.01)
*C07C 309/30* (2006.01)

(52) U.S. Cl.
CPC ......... *G02B 5/223* (2013.01); *G02B 13/0025* (2013.01); *G02B 27/1013* (2013.01)

(56) References Cited

U.S. PATENT DOCUMENTS

| | | | |
|---|---|---|---|
| 9,618,666 | B2 | 4/2017 | Kawashima et al. |
| 9,698,186 | B2 | 7/2017 | Kawashima et al. |
| 10,036,838 | B2 | 7/2018 | Bak et al. |
| 2002/0068778 | A1* | 6/2002 | Ohnishi ............. C08K 5/521 524/140 |
| 2015/0124152 | A1 | 5/2015 | Bak et al. |
| 2015/0138369 | A1 | 5/2015 | Takakuwa et al. |
| 2015/0293283 | A1 | 10/2015 | Nara et al. |
| 2015/0346404 | A1* | 12/2015 | Bak ............. H04N 9/04553 348/342 |

FOREIGN PATENT DOCUMENTS

| | | | | |
|---|---|---|---|---|
| JP | 2001049234 A | * | 2/2001 | ............ C09K 3/00 |
| JP | 2001-213918 A | | 8/2001 | |
| JP | 3206940 B2 | | 9/2001 | |
| JP | WO2005111170 A1 | | 11/2005 | |
| JP | 3939822 B2 | | 7/2007 | |
| JP | 4749388 B2 | | 8/2011 | |
| JP | 5400033 B2 | | 1/2014 | |
| JP | 5953322 B2 | | 7/2016 | |
| JP | 5957022 B2 | | 7/2016 | |
| JP | 6043569 B2 | | 12/2016 | |
| JP | 6110325 B2 | | 4/2017 | |
| JP | 6129763 B2 | | 5/2017 | |
| KR | 100481090 B1 | | 4/2005 | |
| KR | 20150031474 A | | 3/2015 | |
| KR | 20150097618 A | | 8/2015 | |
| KR | 20150143640 A | | 12/2015 | |
| KR | 101658414 B1 | | 9/2016 | |

* cited by examiner

NEAR-INFRARED ABSORBING COMPOSITION, OPTICAL STRUCTURE, AND CAMERA MODULE AND ELECTRONIC DEVICE COMPRISING THE SAME

CROSS-REFERENCE TO RELATED APPLICATION

This application claims priority to and the benefit of Korean Patent Application No. 10-2018-0087193 filed in the Korean Intellectual Property Office on Jul. 26, 2018, the entire contents of which are incorporated herein by reference.

BACKGROUND

1. Field

A near-infrared absorbing composition, an optical structure, and a camera module and an electronic device including the same are disclosed.

2. Description of the Related Art

Recently, an electronic device including an image sensor that stores an image as an electrical signal, such as a cell phone, a digital camera, a camcorder and a camera, has been widely used.

This electronic device may include an optical filter having a near-infrared absorption capability in order to reduce or prevent generation of an optical distortion by light in the other regions than a visible region.

The optical filter is generally mounted in front of an image sensor of a camera module and thus plays a role of effectively absorbing an incident near-infrared ray and resolving the optical distortion phenomenon.

Recently, many attempts to make the optical filter into a thin film have been made according to a requirement of down-sizing and highly integrating an electronic device. However, when the thin-film optical filter is used to observe and take a picture of a high luminance subject, it may cause a flare phenomenon such as a WiFi-type flare phenomenon that an outline is generated around the subject, a petal flare phenomenon that light is irradiated with the subject as the center, and the like.

This flare phenomenon is an optical distortion phenomenon generated when an image sensor in an electronic device recognizes light in a visible wavelength region and infrared to near-infrared wavelength regions together.

Accordingly, in order to reduce and/or minimize the optical distortion phenomenon, light in the near-infrared wavelength region not recognized by human eyes due to a luminosity difference of the human eyes and the image sensor needs to be absorbed or reflected and thus blocked.

SUMMARY

A near-infrared absorbing composition having improved near-infrared absorbance and coating properties, and low visible light absorbance and haze is provided.

In addition, an optical structure formed using the near-infrared absorbing composition and a camera module and an electronic device including the same are provided.

According to an embodiment, a near-infrared absorbing composition includes a copper complex represented by Chemical Formula 1.

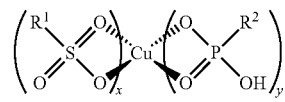

[Chemical Formula 1]

In Chemical Formula 1, $R^1$ and $R^2$ are independently one of hydrogen, deuterium, a substituted or unsubstituted C1 to C20 alkyl group, a substituted or unsubstituted C1 to C20 alkenyl group, a substituted or unsubstituted C1 to C20 alkynyl group, a substituted or unsubstituted C1 to C20 cycloalkyl group, a substituted or unsubstituted C1 to C20 aryl group, a substituted or unsubstituted C1 to C20 heteroaryl group, a photo-polymerizable functional group, $-OR^{a1}$, $-C(=O)R^{a2}$, or $-OC(=O)R^{a3}$ (wherein $R^{a1}$, $R^{a2}$, and $R^{a3}$ are independently one of hydrogen, deuterium, a substituted or unsubstituted C1 to C20 alkyl group, a substituted or unsubstituted C1 to C20 alkenyl group, a substituted or unsubstituted C1 to C20 cycloalkyl group, a substituted or unsubstituted C1 to C20 aryl group, or a substituted or unsubstituted C1 to C20 heteroaryl group), $0 < x \leq 4$, and $0 < y \leq 4$.

In some embodiments, the photo-polymerizable functional group may include a functional group represented by Chemical Formula 11.

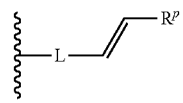

[Chemical Formula 11]

In Chemical Formula 11,

L is one of a single bond, a substituted or unsubstituted C1 to C20 alkylene group, a substituted or unsubstituted C1 to C20 cycloalkylene group, a substituted or unsubstituted C1 to C20 arylene group, a substituted or unsubstituted C1 to C20 heteroarylene group, $-O-$, $-S-$, $-C(=O)-$, or a combination thereof, and $R^p$ is one of hydrogen, deuterium, a substituted or unsubstituted C1 to C20 alkyl group, a substituted or unsubstituted C1 to C20 aryl group, or a substituted or unsubstituted C1 to C20 heteroaryl group.

In some embodiments, at least one of $R^1$ and $R^2$ may be a photo-polymerizable functional group.

In some embodiments, $R^1$ may be one of a substituted or unsubstituted C1 to C20 alkyl group, a substituted or unsubstituted C1 to C20 cycloalkyl group, or a substituted or unsubstituted C1 to C20 aryl group, and $R^2$ may be a photo-polymerizable functional group.

In some embodiments, the copper complex may be represented by Chemical Formula 2.

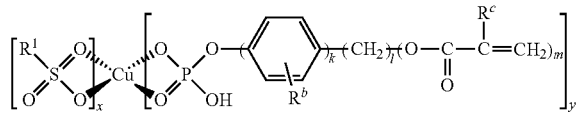

[Chemical Formula 2]

In Chemical Formula 2, $R^1$, x, and y are independently the same as defined in Chemical Formula 1, $R^b$ and $R^c$ are independently one of hydrogen, deuterium, a substituted or unsubstituted C1 to C20 alkyl group, a substituted or unsubstituted C1 to C20 cycloalkyl group, a substituted or unsubstituted C1 to C20 aryl group, or a substituted or unsubstituted C1 to C20 heteroaryl group, k and l are independently an integer ranging from 0 to 8, and m is 0 or 1.

In some embodiments, m may be 1 and one of k and l may be 0.

In some embodiments, m may be 1 and k and l may be independently an integer of 1 to 8.

In some embodiments, the near-infrared absorbing composition may include one or more compounds represented by Chemical Formula 1-1 to Chemical Formula 1-8.

[Chemical Formula 1-1]

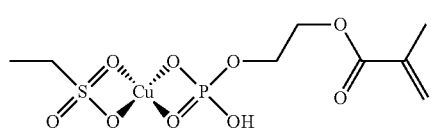

[Chemical Formula 1-2]

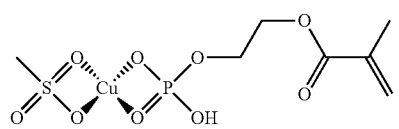

[Chemical Formula 1-3]

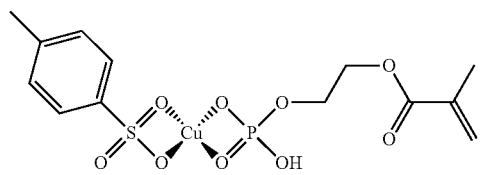

[Chemical Formula 1-4]

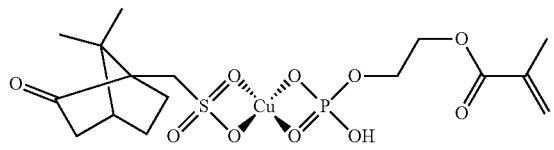

[Chemical Formula 1-5]

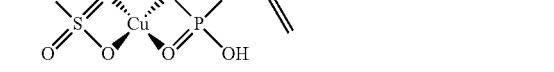

[Chemical Formula 1-6]

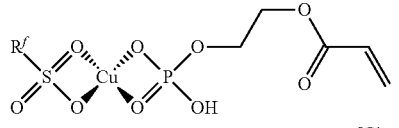

[Chemical Formula 1-7]

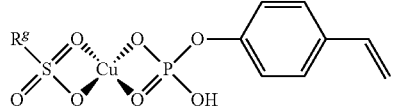

[Chemical Formula 1-8]

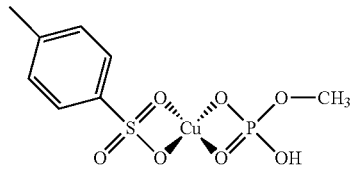

In Chemical Formula 1-1 to Chemical Formula 1-8, $R^e$, $R^f$, and $R^g$ are independently one of hydrogen, deuterium, a substituted or unsubstituted C1 to C20 alkyl group, a substituted or unsubstituted C1 to C20 cycloalkyl group, or a substituted or unsubstituted C1 to C20 aryl group.

In some embodiments, the near-infrared absorbing composition may further include a polymerizable monomer having a thermal polymerization property or a photo-polymerization property, and a solvent.

In some embodiments, the polymerizable monomer may include an acryl-based monomer, an epoxy-based monomer, a vinyl-based monomer, or a combination thereof.

In some embodiments, the solvent may include ethanol, methanol, benzene, toluene, xylene, NMP (N-methylpyrrolidone), acrylonitrile, acetonitrile, THF (tetrahydrofuran), ethyl acetate, MEK (methylethylketone), butylcarbitol, butylcarbitolacetate, butylcellosolve, butylcellosolveacetate, ethylcarbitol, ethylcarbitolacetate, IPA (isopropyl alcohol), acetone, DMF (dimethyl formamide), DMSO (dimethyl sulfoxide), piperidine, phenol, MIBK (methylisobutylketone), PGME (1-methoxy-2-propanol), PGMEA (propylene glycolmonomethyl ether acetate), or a combination thereof.

In some embodiments, the near-infrared absorbing composition may have a maximum absorption wavelength of about 830 nm to about 900 nm.

In some embodiments, the near-infrared absorbing composition may have a cut-off wavelength of about 660 nm to about 700 nm.

According to another embodiment, an optical structure includes a near-infrared absorption layer formed using the near-infrared absorbing composition.

In some embodiments, the copper complex may be included in an amount of about 50 wt % to about 100 wt % based on a total weight of the near-infrared absorption layer.

In some embodiments, the near-infrared absorption layer may further include an acryl-based polymer, an epoxy-based polymer, or a combination thereof.

In some embodiments, the optical structure may have an average light transmittance of greater than or equal to about 80% in a wavelength region of about 430 nm to about 565 nm.

In some embodiments, the optical structure may have an average light transmittance of less than or equal to about 15% in a wavelength region of about 740 nm to about 950 nm.

In some embodiments, the optical structure may have an average light transmittance of less than or equal to about 25% in a wavelength region of about 700 nm to about 740 nm.

In some embodiments, the optical structure may have a haze of greater than 0% and less than or equal to about 3% in a wavelength region of about 435 nm to about 565 nm.

According to another embodiment, a camera module includes a lens; an image sensor; and the optical structure disposed between the lens and the image sensor and/or an electronic device includes the optical structure.

The near-infrared absorbing composition according to an embodiment has improved near-infrared absorbance and low visible absorbance and thus may minimize the optical distortion and obtain a vivid image, has a low haze in a visible light wavelength region, and may form an optical structure having high coating properties and reliability.

In addition, a camera module and an electronic device including the optical structure according to an embodiment may provide an image having a minimized optical distortion.

DETAILED DESCRIPTION

Figure 1:
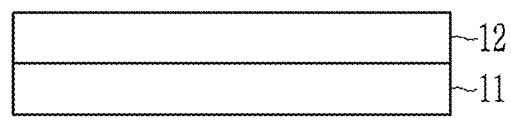
FIG. 1 is a schematic cross-sectional view showing an optical structure according to an embodiment.

Hereinafter, example embodiments of the present disclosure will be described in detail so that a person skilled in the art would understand the same. This disclosure may, however, be embodied in many different forms and is not construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

Hereinafter, a near-infrared absorbing composition according to an embodiment is described.

The near-infrared absorbing composition according to an embodiment includes a copper complex represented by Chemical Formula 1.

[Chemical Formula 1]

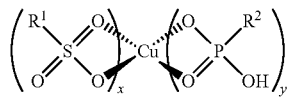

In Chemical Formula 1, $R^1$ and $R^2$ are independently one of hydrogen, deuterium, a substituted or unsubstituted C1 to C20 alkyl group, a substituted or unsubstituted C1 to C20 alkenyl group, a substituted or unsubstituted C1 to C20 alkynyl group, a substituted or unsubstituted C1 to C20 cycloalkyl group, a substituted or unsubstituted C1 to C20 aryl group, a substituted or unsubstituted C1 to C20 heteroaryl group, a photo-polymerizable functional group, $-OR^{a1}$, $-C(=O)R^{a2}$, or $-OC(=O)R^{a3}$ (wherein $R^{a1}$, $R^{a2}$, and $R^{a3}$ are independently one of hydrogen, deuterium, a substituted or unsubstituted C1 to C20 alkyl group, a substituted or unsubstituted C1 to C20 alkenyl group, a substituted or unsubstituted C1 to C20 cycloalkyl group, a substituted or unsubstituted C1 to C20 aryl group, or a substituted or unsubstituted C1 to C20 heteroaryl group), $0 < x \leq 4$, and $0 < y \leq 4$.

That is, in the near-infrared absorbing composition according to an embodiment, heterogeneous acid group ligands form a coordination bond with copper respectively, as shown in Chemical Formula 1.

On the other hand, the photo-polymerizable functional group may include a functional group represented by Chemical Formula 11.

[Chemical Formula 11]

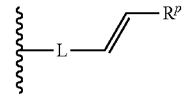

In Chemical Formula 11,

L is one of a single bond, a substituted or unsubstituted C1 to C20 alkylene group, a substituted or unsubstituted C1 to C20 cycloalkylene group, a substituted or unsubstituted C1 to C20 arylene group, a substituted or unsubstituted C1 to C20 heteroarylene group, $-O-$, $-S-$, $-C(=O)-$, or a combination thereof, and $R^p$ is one of hydrogen, deuterium, a substituted or unsubstituted C1 to C20 alkyl group, a substituted or unsubstituted C1 to C20 aryl group, or a substituted or unsubstituted C1 to C20 heteroaryl group.

In an embodiment, at least one of $R^1$ and $R^2$ may be a photo-polymerizable functional group. For example, $R^1$ may be one of a substituted or unsubstituted C1 to C20 alkyl group, a substituted or unsubstituted C1 to C20 cycloalkyl group, or a substituted or unsubstituted C1 to C20 aryl group and $R^2$ may be a photo-polymerizable functional group.

Like this, when the copper complex according to an embodiment includes a photo-polymerizable functional group, a film formed using the near-infrared absorbing composition may have improved coating properties and coating stability. On the other hand, when the copper complex has no photo-polymerizable functional group, gradual crystallization by an intermolecular interaction may occur only by thermal energy of room temperature, and thus visible rays may be scattered and a film having a high haze may be produced.

However, an embodiment is not limited thereto, $R^1$ and $R^2$ may be the photo-polymerizable functional group represented by Chemical Formula 11, one of $R^1$ and $R^2$ may be another photo-polymerizable functional group that is different from Chemical Formula 11. Alternatively, both of $R^1$ and $R^2$ may not be a photo-polymerizable functional group.

On the other hand, in the copper complex according to an embodiment, when at least $R^2$ is a photo-polymerizable functional group, the copper complex may be represented by Chemical Formula 2.

[Chemical Formula 2]

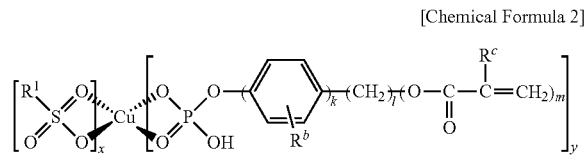

In Chemical Formula 2, $R^1$, x, and y are the same as in Chemical Formula 1, $R^b$ and $R^c$ are independently one of hydrogen, deuterium, a substituted or unsubstituted C1 to C20 alkyl group, a substituted or unsubstituted C1 to C20 cycloalkyl group, a substituted or unsubstituted C1 to C20 aryl group, or a substituted or unsubstituted C1 to C20 heteroaryl group, k and l are independently an integer ranging from 0 to 8, and m is 0 or 1.

In an embodiment, m may be 1 and one of k and l may be 0. In an embodiment, m may be 1 and k and l may independently be an integer of 1 to 8.

That is, the copper complex represented by Chemical Formula 2 has at least acrylate-based photo-polymerizable functional group and may control a kind and a length of a moiety linked with a phosphate-based acid group.

The near-infrared absorbing composition including the copper complex may include at least one of compounds represented by Chemical Formula 1-1 to Chemical Formula 1-8.

[Chemical Formula 1-1]

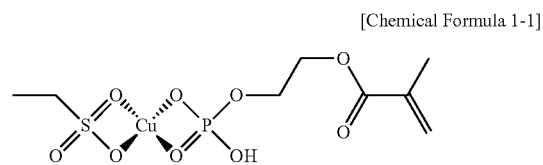

[Chemical Formula 1-2]

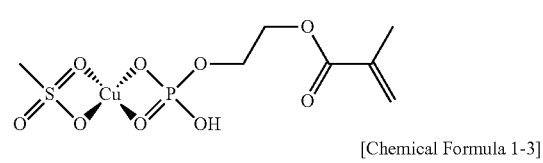

[Chemical Formula 1-3]

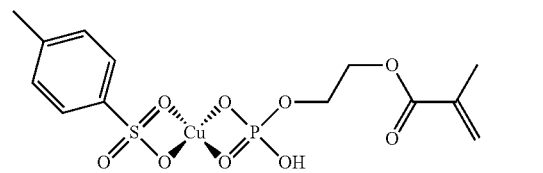

[Chemical Formula 1-4]

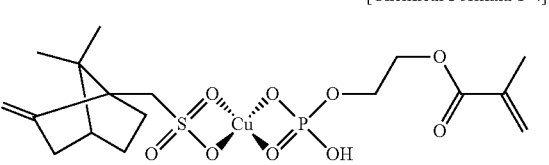

[Chemical Formula 1-5]

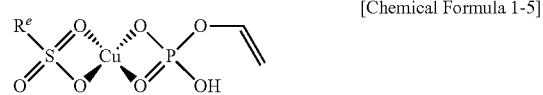

[Chemical Formula 1-6]

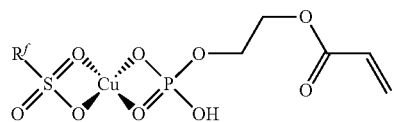

[Chemical Formula 1-7]

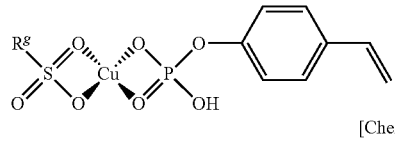

[Chemical Formula 1-8]

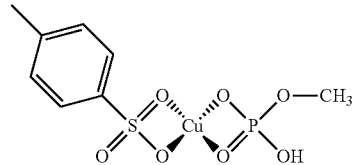

In Chemical Formula 1-1 to Chemical Formula 1-8, $R^e$, $R^f$, and $R^g$ are independently one of hydrogen, deuterium, a substituted or unsubstituted C1 to C20 alkyl group, a substituted or unsubstituted C1 to C20 cycloalkyl group, or a substituted or unsubstituted C1 to C20 aryl group.

The near-infrared absorbing composition according to an embodiment may further include a thermally or photo-cross-linkable monomer and a solvent.

In an embodiment, the cross-linkable monomer may have a photo-polymerization property, and in this case, the near-infrared absorbing composition may further include an additive for initiating a photo-polymerization reaction between monomers, for example a photoinitiator. However, the embodiment is not limited thereto, the polymerizable monomer may have a thermal polymerization property, and the near-infrared absorbing composition may include a different polymer binder from the polymerizable monomer, a surfactant, an antioxidizing agent, and the like as an additive.

In an embodiment, the solvent may be an organic solvent. Examples of the organic solvent may be ethanol, methanol, benzene, toluene, xylene, NMP (N-methylpyrrolidone), acrylonitrile, acetonitrile, THF (tetrahydrofuran), ethyl acetate, MEK (methylethylketone), butylcarbitol, butylcarbitolacetate, butylcellosolve, butylcellosolveacetate, ethylcarbitol, ethylcarbitolacetate, IPA (isopropylalcohol), acetone, DMF (dimethyl formamide), DMSO (dimethylsulfoxide), piperidine, phenol, MIBK (methylisobutylketone), PGME (1-methoxy-2-propanol), PGMEA (propylene glycolmonomethyl ether acetate), or a combination thereof. That is, the copper complex according to an embodiment may ensure solubility groups of the organic solvent or a combination thereof.

The near-infrared absorbing composition according to an embodiment may further include a thermally or photo-cross-linkable monomer. Examples of the cross-linkable monomer may be an acryl-based monomer, an epoxy-based monomer, or a combination thereof. The cross-linkable monomer may be an polymerizable cross-linkable monomer. The cross-linkable monomer may perform a binder function, when the near-infrared absorbing composition is used to form a near-infrared absorption layer.

On the other hand, the near-infrared absorbing composition according to an embodiment may further include an organic dye having near-infrared absorption capability in addition to the copper complex. Examples of the organic dye may include a squarylium-based compound, a cyanine-based compound, a phthalocyanine-based compound, a thiophene-based compound, a diimmonium-based compound, or a combination thereof.

The organic dye has a narrower line width of a near-infrared absorption wavelength is narrower than that of the copper complex and thus may be used together with the copper complex, when absorption capability regarding light in a particularly narrow wavelength region, for example about 700 nm to about 740 nm among near-infrared rays needs to be complemented. In other words, the near-infrared absorbing composition according to an embodiment may further include at least one kind of organic dye having absorption capability regarding light in a particular near-infrared ray wavelength region requiring of the complement along with the copper complex.

A near-infrared filter absorbing and/or reflecting light of a near-infrared wavelength may be largely classified into a glass type and a film type.

The glass type filter in general uses a near-infrared reflection layer formed by at least twice alternately disposing a titanium oxide and a silicon oxide, is inexpensive, and has high near-infrared reflection efficiency with respect to incident light from its front side. However, this glass type filter has a problem of increasing an internal reflection with respect to incident light from its side, and accordingly, in order to compensate this problem, a glass material using the near-infrared reflection layer and a near-infrared absorption material together has been suggested.

This near-infrared absorption material may secure an absorbance wavelength by controlling a 'boundary wavelength' between a visible light wavelength region and a near-infrared ray. The 'boundary wavelength' is defined as a wavelength transmitting 50% of light in the visible light wavelength region but absorbing 50% of the light in the same region and referred to be a cut-off wavelength hereinafter.

The cut-off wavelength may be changed depending on an absorption band width and a maximum absorption wavelength of the near-infrared absorption material. The near-infrared absorption material and particularly, a copper complex has a wide absorption band of about 600 nm to about 1200 nm, which is caused due to delocalization of a d orbital having a triplet state, and experimentally, the absorption band width may have a similar tendency depending on a material. Accordingly, the cut-off wavelength is determined by a maximum absorption wavelength of the copper complex, which may vary depending on a structure and a kind of a ligand determining a HOMO (highest occupied molecular orbital) energy and an LUMO (lowest unoccupied molecular orbital) energy of copper.

In general, a copper complex used for near-infrared absorption has a structure where one kind of (homogeneous) a ligand, for example a homogeneous sulfate-based ligand or a homogeneous phosphate ligand forms a coordination bond with the copper. However, when a film is formed of a composition including a conventional copper complex, the cut-off wavelength may be about 630 nm to about 650 nm and may be overlapped with a part of the visible light wavelength region (red wavelength region). In this case, the film may reduce visual information of a red wavelength region and may provide a strong blue image (distorted color image).

However, in the near-infrared absorbing composition according to an embodiment, the copper complex includes different two kinds of ligands (P-based acid group ligand and S-based acid group ligand) simultaneously, and thus a maximum absorption wavelength of the copper complex may be shifted into a long wavelength.

Accordingly, a copper complex having two kinds of ligands like the copper complex according to an embodiment may adjust a maximum absorption wavelength of a near-infrared absorbing composition within a particular range, for example, of greater than or equal to about 830 nm, greater than or equal to about 832 nm, or greater than or equal to about 834 nm, and less than or equal to about 900 nm, less than or equal to about 880 nm, less than or equal to about 860 nm, for example about 830 nm to about 900 nm or about 830 nm to about 860 nm.

Accordingly, the cut-off wavelength of the near-infrared absorbing composition according to an embodiment may be adjusted to be greater than or equal to about 660 nm, greater than or equal to about 662 nm, greater than or equal to about 664 nm, or greater than or equal to about 700 nm, and less than or equal to about 690 nm, or less than or equal to about 680 nm, or about 660 nm to about 700 nm, for example about 660 nm to about 690 nm, by adjusting the maximum absorption wavelength.

That is, the near-infrared absorbing composition according to an embodiment and the film manufactured using the same show cut-off wavelengths that are shifted to a long wavelength, and thus an image without color distortion may be obtained.

On the other hand, when a film is formed of a conventional copper complex having one kind of a ligand described above, amorphous characteristics of the film may cause crystallization by heating during a coating process and thus a haze may be increased. That is, a film using the conventional copper complex has unfavorable coating properties. In this case, it may be impossible that titanium oxide and silicon oxide are deposited on the film to be used as a glass material.

On the contrary, the near-infrared absorbing composition includes the photo-polymerizable functional group as a substituent of the ligand, and thereby the photo-polymerizable functional group may fix cooper in order to not cause unnecessary hazes by heating during the coating process. Accordingly, a film formed of the near-infrared absorbing composition according to an embodiment may have improved visible light transmittance and coating properties even if it is formed into a film.

Hereinafter, an optical structure according to an embodiment, that is, an optical structure including a near-infrared absorption layer manufactured using the composition is described with reference to drawings.

FIG. 1 is a schematic cross-sectional view showing an optical structure according to another embodiment.

Referring to FIG. 1, an optical structure 10 includes a near-infrared absorption layer 12. In an embodiment, one example of the optical structure 10 illustrates the near-infrared absorption layer 12 formed on a transparent substrate 11. However, the present scope is not necessarily limited thereto. For example, in some embodiments, the optical structure may be formed directly on an image sensor, not on a transparent substrate, or may be a film structure (e.g., thin-film structure) having a surface covered with a release paper or the like.

Also, the near-infrared absorption layer 12 may be formed as a monolayer or a multilayer of at least two layers, and the near-infrared absorption layer 12, and another layer performing near-infrared absorption and/or reflection may be included therein.

In an embodiment, the transparent substrate 11 may be made of an optically transparent substrate and may have, for example, an average light transmittance of greater than or equal to about 80%, greater than or equal to about 85%, or greater than or equal to about 90% in a visible region. Herein, the visible region may be for example a wavelength region of greater than about 380 nm and less than about 700 nm and the average light transmittance is an average value of light transmittance measured when incident light is radiated in a vertical direction (front direction) of the transparent substrate 11.

The transparent substrate 11 may include, for example glass, polyethyleneterephthalate, triacetyl cellulose, polycarbonate, a cycloolefin polymer, poly(meth)acrylate, polyimide, polystyrene, or a combination thereof, but is not limited thereto.

The transparent substrate 11 may selectively absorb at least one part of light in an ultraviolet (UV) region. Ultraviolet (UV) absorption capability of the transparent substrate 11 may be caused by a material itself of the transparent substrate 11, but the transparent substrate 11 having ultraviolet (UV) absorption capability may be formed by adding an ultraviolet (UV) absorber thereto. Herein, the ultraviolet (UV) region may be, for example, a wavelength region of less than or equal to about 380 nm.

The transparent substrate 11 may absorb most of light in a wavelength region of at least about 350 nm to about 380 nm, and thus an average light transmittance of the optical structure 10 in a wavelength region of about 350 nm to about 380 nm may be less than or equal to about 1%, less than or equal to about 0.8%, or less than or equal to about 0.5%.

The transparent substrate 11 may include various additives according to desirable properties of the optical structure 10.

The transparent substrate 11 may have a thickness of about 20 μm to about 120 μm.

The transparent substrate 11 may be formed as a multilayer of at least two layers if needed, or omitted.

The near-infrared absorption layer 12 is configured to transmit light in a visible region and to selectively absorb at least one part of light in a near-infrared region. Herein, the visible region may be for example a wavelength region of greater than about 380 nm and less than about 700 nm and the near-infrared region may be for example a wavelength region of about 700 nm to about 1200 nm.

The near-infrared absorption layer 12 includes the copper complex and may further include a thermally or photo-crosslinkable polymer, a surfactant, an antioxidizing agent, a photoinitiator, and the like.

In an embodiment, the copper complex in the near-infrared absorption layer 12 may be included in an appropriate amount so that the near-infrared absorption layer 12 may have a desirable near-infrared absorption capability. In an embodiment, the copper complex may be for example included in an amount of greater than or equal to about 60 wt %, greater than or equal to about 65 wt %, greater than or equal to about 70 wt %, greater than or equal to about 75 wt %, greater than or equal to about 80 wt %, greater than or equal to about 85 wt %, greater than or equal to about 90 wt %, greater than or equal to about 95 wt %, or even about 100 wt % (the near-infrared absorption layer consists of the copper complex) based on the total weight of the near-infrared absorption layer 12.

In an embodiment, the thermally or photo-cross-linkable polymer may be prepared by polymerizing a polymerizable monomer included in the above near-infrared absorbing film by heat or light. Examples of the polymer may be an acryl-based polymer, an epoxy-based polymer, or a combination thereof.

The near-infrared absorption layer 12 may be formed by coating the near-infrared absorbing composition on the transparent substrate 11 and polymerizing the thermally or photo-cross-linkable monomer. In other words, the near-infrared absorption layer 12 may be formed through a polymerization reaction of the polymerizable monomer in the near-infrared absorbing composition.

The polymerization reaction may be different depending on characteristics of the polymerizable monomer forming the polymer, for example, performed by heat and/or light.

The composition coated on the transparent substrate 11 may be selectively curable by heat and/or light and the coating may be for example a spin coating, a slit coating, a bar coating, a blade coating, a slot die coating, and/or an inkjet coating.

The near-infrared absorption layer 12 of the optical structure 10 may have, for example a thickness of about 10 μm to about 200 μm, for example about 50 μm to about 200 μm, or about 50 μm to about 150 μm. Within the thickness ranges, the optical structure 10 may realize performance of an optical filter.

However, inventive concepts are not necessarily limited thereto, a thickness of the near-infrared absorption layer 12 may be variously set with a consideration to presence and a kind of other organic dyes for near-infrared absorption in addition to the copper complex and their relationship with other constituent elements consisting of the optical structure, for example, a transparent substrate, an infrared reflection layer, and the like.

The optical structure 10 according to the present embodiment transmits light in a visible region effectively and blocks light in a near-infrared region effectively even if the transparent substrate 11 and the near-infrared absorption layer 12 are sequentially stacked.

In addition, light in an ultraviolet (UV) region may be effectively blocked by imparting an absorption function of light in an ultraviolet (UV) region to the transparent substrate 11. Accordingly, the optical structure 10 may effectively sense light in a visible region in a sensor sensing light such as an image sensor by increasing purity of transmittance of light in a visible region of light in all wavelength regions and thus optical distortion by light besides the visible region may be decreased or prevented.

For example, the optical structure 10 may have an average light transmittance of greater than or equal to about 80%, for example greater than or equal to about 83%, or greater than or equal to about 85%, and less than or equal to about 93%, for example less than or equal to about 90%, or less than or equal to about 88% in a wavelength region of about 435 nm to about 565 nm. In addition, the optical structure 10 may have an average light transmittance of less than or equal to about 15%, for example less than or equal to about 14%, or less than or equal to about 13.5% in a wavelength region of about 740 nm to about 950 nm, an average light transmittance of less than or equal to about 25%, for example less than or equal to about 10%, or less than or equal to about 5% in a wavelength region of about 700 nm to about 740 nm, and an average light transmittance of less than or equal to about 40%, for example less than or equal to about 20% in a wavelength region of about 950 nm to about 1100 nm.

On the other hand, the optical structure 10 according to an embodiment may have a haze of less than or equal to about 5%, less than or equal to about 4%, less than or equal to about 3%, less than or equal to about 2%, or less than or equal to about 1%, for example greater than 0% and less than or equal to about 3%, or greater than 0% and less than or equal to about 2% in a wavelength region of about 435 nm to about 565 nm.

The average light transmittance is an average value of light transmittance measured when incident light is radiated in a vertical direction (front direction) of the optical structure 10.

In this way, the optical structure 10 selectively absorbs and thus blocks light in a near-infrared wavelength region corresponding to a boundary between a visible region and an infrared region out of all the wavelength region and thus reduces or prevents crossing and mingling of a signal by light in a visible region with a signal by light in a nonvisible region and resultantly, may reduce or prevent an optical distortion such as a crosstalk.

In addition, the optical structure 10 according to an embodiment includes a photo-polymerizable functional group as a ligand as described above, a haze in a visible light wavelength region may be controlled to be very low by lowering crystallinity and fixing an amorphous state.

On the other hand, the optical structure 10 may effectively absorb light in a near-infrared region regardless of an incident direction and accordingly, effectively absorb and block incident light in a near-infrared region from a side direction and thus reduce or prevent the incident light in a near-infrared region from a side direction from distorting the signal of visible light.

In addition, the optical structure 10 may show improved near-infrared absorbance and low visible absorbance due to the above near-infrared absorbing composition. Furthermore, the optical structure 10 shows excellent coating properties as described above and also, excellent high temperature reliability about optical properties of the formed near-infrared absorption layer 12.

Figure 2:
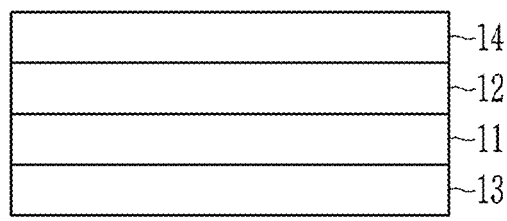
FIG. 2 is a schematic cross-sectional view showing an optical structure according to another embodiment.

FIG. 2 is a schematic cross-sectional view showing an optical structure according to one example variation.

Referring to FIG. 2, the optical structure 10 according to one example variation includes a transparent substrate 11, a near-infrared absorption layer 12, and infrared reflection layers 13 and 14.

The transparent substrate 11 and the near-infrared absorption layer 12 are the same as described above.

The infrared reflection layers 13 and 14 may be disposed on at least one of one surface of the transparent substrate and one surface of the near-infrared absorption layer. For example, the infrared reflection layers 13 and 14 may be disposed under the transparent substrate 11 and/or on the near-infrared absorption layer 12. In the view, the infrared reflection layers 13 and 14 are shown, but either of them may be omitted.

The infrared reflection layers 13 and 14 effectively reflect light in an infrared wavelength region and thus may effectively reduce or prevent optical distortion by the light in an infrared wavelength region.

The infrared reflection layers 13 and 14 may reflect light in a mid-infrared region, a far-infrared region, and a part of a near-infrared region, for example, a wavelength region of about 700 nm to about 3 μm.

The infrared reflection layers 13 and 14 are not particularly limited as long as they reflect light in an infrared wavelength region and may be, for example a high refractive index reflective layer, a reflective layer including a high refractive index nanoparticle, or a multilayer including a plurality of layers having different refractive indexes, but is not limited thereto.

For example, the infrared reflection layers 13 and 14 may include a first layer and a second layer consisting of materials having different refractive indexes, and may include a multilayer where the first layer and the second layer are alternately and repeatedly stacked.

The first layer and the second layer may be, for example a dielectric layer including an oxide layer, a nitride layer, an oxynitride layer, a sulfide layer, or a combination thereof, and for example the first layer may have a refractive index of less than about 1.7 and the second layer may have a refractive index of greater than or equal to about 1.7. Within the ranges, for example the first layer may have a refractive index of greater than or equal to about 1.1 and less than about 1.7 and the second layer may have a refractive index about 1.7 to about 2.7, or for example the first layer may have a refractive index of about 1.2 to about 1.6 and the second layer may have a refractive index of about 1.8 to about 2.5.

The first layer and the second layer may include any material having the refractive indexes within the ranges, and for example the first layer may include a silicon oxide, an aluminum oxide, or a combination thereof and the second layer may include titanium oxide, zinc oxide, indium oxide, zirconium oxide, or a combination thereof. The first layer and the second layer may be, for example five-layered to 80-layered, for example 5-layered to 50-layered.

Thicknesses of the first layer and the second layer may be determined according to a refractive index and a reflection wavelength of each layer, for example each of the first layer may have a thickness of about 10 nm to about 700 nm and each of the second layer may have a thickness of about 30 nm to about 600 nm. Thicknesses of the first layer and the second layer may be the same or different.

The optical structure 10 may have, for example a thickness of 10 μm to about 200 μm. Within the ranges of the thickness, an infrared absorption optical filter may be realized.

The optical structure 10 according to the present embodiment includes the transparent substrate 11 and the near-infrared absorption layer 12 like the above embodiment and transmits light in a visible region effectively and blocks light in a near-infrared region effectively. In addition, the optical structure 10 according to the embodiment further includes infrared reflection layers 13 and 14, thereby effectively blocks light in a mid-infrared region and a far-infrared region by reflecting them, and thus may be effectively used as an optical filter preventing transmittance of light in all the infrared regions. Accordingly, the optical structure 10 may be applied to an electronic device and thus may reduce or prevent distortion of an optical signal in a visible region by light in the infrared region.

The optical structure 10 may be applied to all uses for filtering light in an infrared or near-infrared wavelength region, and may be, for example applied to a camera module and an electronic device including the same. The electronic device may be a digital camera, a camcorder, a monitoring camera such as CCTV, an in-car camera, a medical camera, a cell phone having a built-in or external camera, a computer having a built-in or external camera, a laptop computer having a built-in or external camera, and the like but is not limited thereto.

Figure 3:
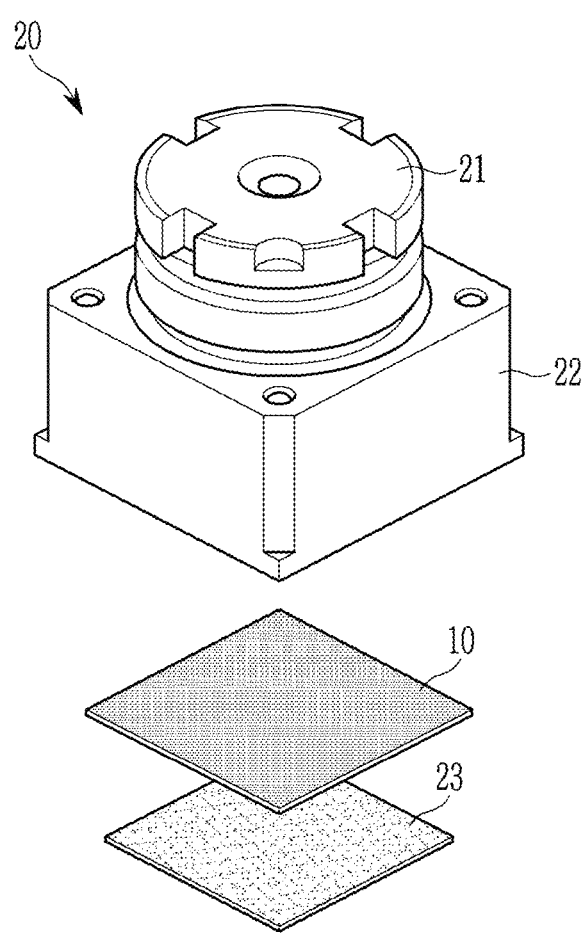
FIG. 3 is a schematic view showing a camera module according to an embodiment.

FIG. 3 is a schematic view of a camera module according to an embodiment.

Referring to FIG. 3, a camera module 20 includes a lens barrel 21, a housing 22, an optical structure 10, and an image sensor 23.

The lens barrel 21 includes at least one lens for imaging a subject, and the lens may be disposed along an optical axis direction. Herein, the optical axis direction may be a vertical direction of the lens barrel 21.

The lens barrel 21 is internally housed in the housing 22 and united with the housing 22. The lens barrel 21 may be moved in optical axis direction inside the housing 22 for autofocusing.

The housing 22 supports and houses the lens barrel 21 and may be open in the optical axis direction. Accordingly, incident light from one surface of the housing 22 may reach the image sensor 23 through the lens barrel 21 and the optical structure 10.

The housing 22 may be equipped with an actuator for moving the lens barrel 21 in the optical axis direction. The actuator may include a voice coil motor (VCM) including a magnet and a coil. However, various methods such as a mechanical driving system or a piezoelectric driving system using a piezoelectric device other than the actuator may be adopted.

The optical structure 10 is the same as described above.

The image sensor 23 may concentrate an image of a subject and thus store it as data, and the stored data may be displayed as an image through a display media.

The image sensor 23 may be mounted in a substrate (not shown) and electrically connected to the substrate. The substrate may be, for example, a printed circuit board (PCB) or electrically connected to a printed circuit board, and the printed circuit may be, for example, a flexible printed circuit (FPCB).

The image sensor 23 concentrates light passing the lens barrel 21 and the optical structure 10 and generates a video signal and may be a complementary metal-oxide semiconductor (CMOS) image sensor and/or a charge coupled device (CCD) image sensor.

Figure 4:
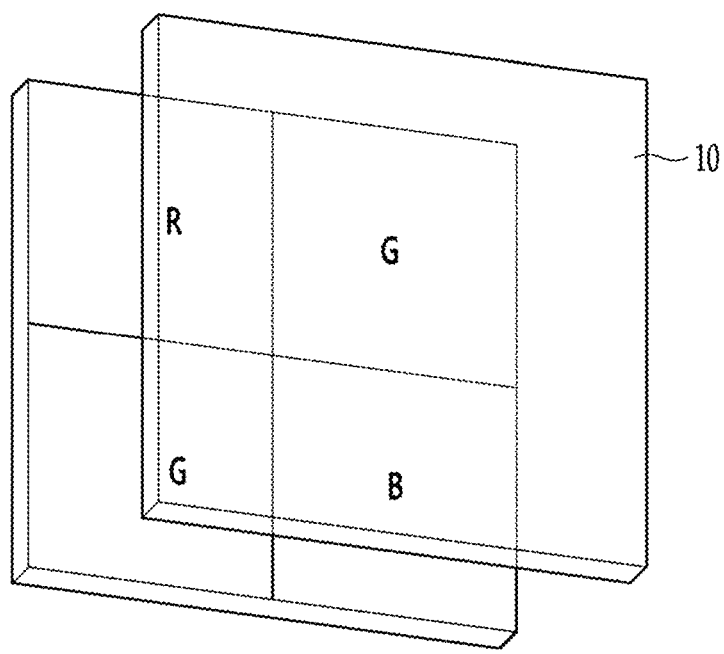
FIG. 4 is a top plan view showing an organic image sensor as one example of an image sensor.

FIG. 4 is a top plan view showing an organic image sensor as one example of an image sensor.

Referring to FIG. 4, the organic image sensor may be formed by arranging a red organic photoelectric device, a green organic photoelectric device, and a blue organic photoelectric device as Bayer shape in a monolayer on an optical structure, as shown in FIG. 4.

However, an embodiment is not necessarily limited thereto, a detailed structures of organic image sensors may be variously set with a kind of materials and structures of the optical structure, and the like.

Figure 5:
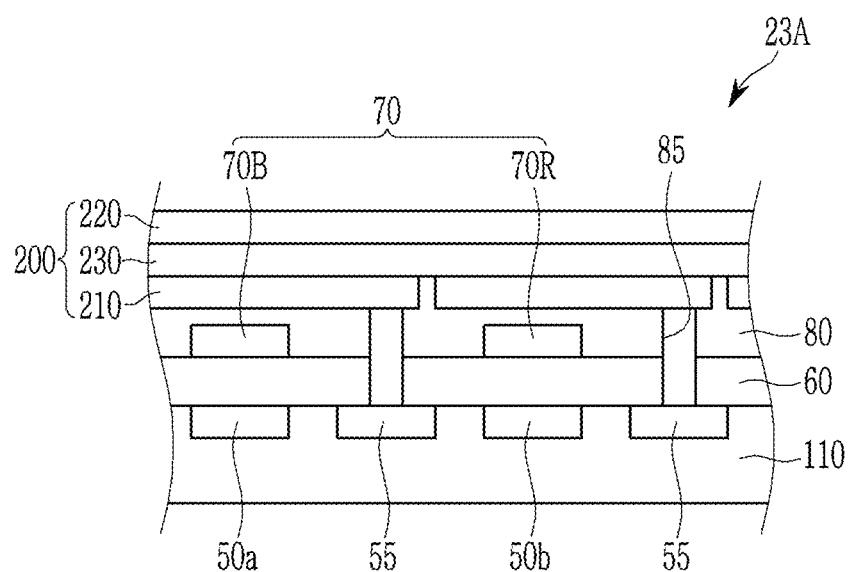
FIG. 5 is a cross-sectional view showing another example of the organic image sensor.

FIG. 5 is a cross-sectional view showing another example of the organic CMOS image sensor, Referring to FIG. 5, an organic image sensor 23A according to an embodiment includes a semiconductor substrate 110 integrated with photo-sensing devices 50*a* and 50*b*, a transmission transistor (not shown), and a charge storage 55, a lower insulation layer 60, a color filter layer 70, a upper insulation layer 80, and an organic photoelectric device 200.

The semiconductor substrate 110 may be a silicon substrate, and is integrated with the photo-sensing devices 50*a* and 50*b*, the transmission transistor (not shown), and the charge storage 55. The photo-sensing devices 50*a* and 50*b* may be photodiodes.

The photo-sensing devices 50*a* and 50*b* sense light, the information sensed by the photo-sensing devices may be transferred by the transmission transistor, the charge storage 55 is electrically connected to the organic photoelectric device 100, and the information of the charge storage 55 may be transferred by the transmission transistor.

The photo-sensing devices 50*a* and 50*b* sense light, the information sensed by the photo-sensing devices may be transferred by the transmission transistor, the charge storage 55 is electrically connected to the organic photoelectric device 100, and the information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but is not limited thereto. However, it is not limited to the structure, and the metal wire and pad may be disposed under the photo-sensing devices 50*a* and 50*b*.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70*a* formed in the blue pixel and a red filter 70*b* formed in the red pixel. In the present embodiment, a green filter is not included, but a green filter may be further included.

The upper insulation layer 80 is formed on the color filter layer 70. The upper insulation layer 80 eliminates a step caused by the color filter layer 70 and smoothes the surface. The upper insulation layer 80 and lower insulation layer 60 may include a contact hole (not shown) exposing a pad, and a through-hole 85 exposing the charge storage 55 of a green pixel.

The organic photoelectric device 200 is formed on the upper insulation layer 80. The organic photoelectric device 200 includes a lower electrode 210 and an upper electrode 220 facing each other and an absorption layer 230 disposed between the lower electrode 210 and the upper electrode 220.

The lower electrode 210 and the upper electrode 220 may be all light-transmitting electrodes and the absorption layer 230 may selectively absorb light in a green wavelength region and may replace a color filter of a green pixel.

In this way, the semiconductor substrate 110 and the organic photoelectric device 200 selectively absorbing light in a green wavelength region have a stack structure and thereby the size of an image sensor may be reduced to realize a down-sized image sensor.

Focusing lens (not shown) may be further formed on the organic photoelectric device 200. The focusing lens may control a direction of incident light and gather the light in one region. The focusing lens may have a shape of, for example, a cylinder or a hemisphere, but is not limited thereto.

In FIG. 5, a structure where the organic photoelectric device selectively absorbing light in a green wavelength region is stacked on the semiconductor substrate 110 is illustrated, but the present disclosure is not limited thereto. An organic photoelectric device selectively absorbing light in a blue wavelength region may be stacked on the semiconductor substrate 110 and a green photo-sensing device and a red photo-sensing device may be integrated in the semiconductor substrate 110 or an organic photoelectric device selectively absorbing light in a red wavelength region may be stacked on the semiconductor substrate 110 and a green photo-sensing device and a blue photo-sensing device may be integrated in the semiconductor substrate 110.

Among the light in a visible region passing the lens barrel 21 and the optical structure 10, light in a green wavelength region may be mainly absorbed in the absorption layer 30 and photoelectrically converted, and light in a blue wavelength region and a red wavelength region may pass the lower electrode 210 and be sensed by the photo-sensing devices 50a and 50b.

As described above, the optical structure 10 has improved near-infrared absorbance, and low visible absorbance and a haze and thereby may transfer pure light in a visible region to an image sensor and resultantly, reduce or prevent a crosstalk generated when a signal by light in a visible region and a signal by light in a non-visible region are crossed and mixed in. Accordingly, an optical distortion phenomenon of the image sensor may be minimized and clear image may be obtained.

Hereinafter, embodiments are described in more detail with reference to examples. However, these examples are non-limiting, and the present scope is not limited thereto.

Preparation of Copper Complex

Preparation Example 1

10 g of copper (II) acetate (Alfa) is dissolved in a tetrahydrofuran solvent using a magnetic stirrer, 11.57 g of phosphoric acid 2-hydroxy metacryl ester (Sigma-Aldrich) is added thereto, and the mixture is reacted at room temperature for 1 day. 6.06 g of ethyl sulfonic acid (Sigma-Aldrich) is added to the reaction solution, and the mixture is reacted at room temperature for 1 day. Non-reacted particles in the reaction solution are removed through a syringe filter, about ½ of tetrahydrofuran is removed with a rotary evaporator, and a precipitate is obtained therefrom by using hexane, and filtered, and dried at room temperature (10° C. to 30° C.) to 50° C. in a vacuum oven for 12 hours to prepare a copper complex represented by Chemical Formula 1-1.

[Chemical Formula 1-1]

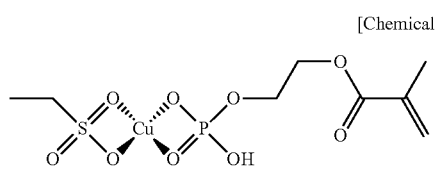

Preparation Example 2

A copper complex represented by Chemical Formula 1-2 is prepared according to the same method as Preparation Example 1 except for using 10 g of copper acetate, 11.57 g of phosphoric acid 2-hydroxy metacryl ester (Sigma-Aldrich), and 5.29 g of methane sulfonic acid.

[Chemical Formula 1-2]

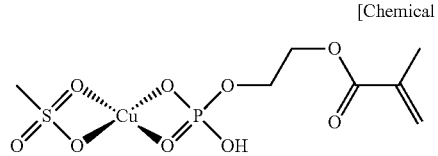

Preparation Example 3

A copper complex represented by Chemical Formula 1-3 is prepared according to the same method as Preparation Example 1 except for using 10 g, 11.57 g of phosphoric acid 2-hydroxy metacryl ester (Sigma-Aldrich), and 10.47 g of paratoluene sulfonic acid (Daejung Chemicals & Metals Co., Ltd.).

[Chemical Formula 1-3]

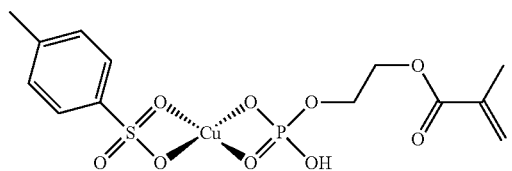

Preparation Example 4

A copper complex represented by Chemical Formula 1-8 is prepared according to the same method as Preparation Example 1 except for using 10 g of copper acetate, 10.47 g of paratoluene sulfonic acid (Daejung Chemicals & Metals Co., Ltd.), and 6.06 g of methyl phosphate (TCI Inc., mono/di mixture).

[Chemical Formula 1-8]

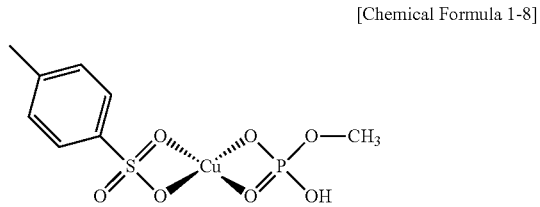

Comparative Preparation Example 1

A copper complex represented by Chemical Formula A is prepared according to the same method as Preparation Example 1 except for using 10 g of copper acetate and 23.14 g of phosphoric acid 2-hydroxy metacryl ester (Sigma-Aldrich).

[Chemical Formula A]

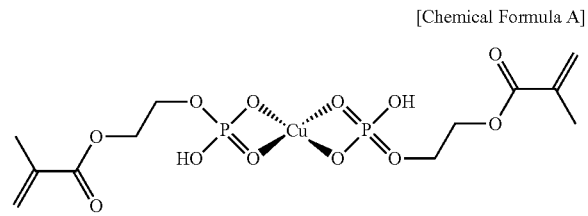

Comparative Preparation Example 2

A copper complex represented by Chemical Formula B is prepared according to the same method as Preparation Example 1 except for using 10 g of copper acetate and 11.57 g of phosphoric acid 2-hydroxy metacryl ester (Sigma-Aldrich).

[Chemical Formula B]

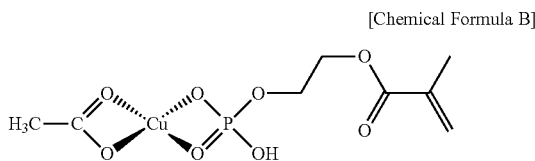

Preparation of Near-Infrared Absorbing Composition

Example 1 to Example 4

Each copper complex according to Preparation Example 1 to Preparation Example 4 is added to ethanol to be a concentration of 10 mg/mL and mixed to prepare near-infrared absorbing compositions according to Example 1 to Example 4.

Comparative Examples 1 and 2

Each near-infrared absorbing composition according to Comparative Example 1 and Comparative Example 2 is prepared according to the same method as Example 1 except for using the copper complexes according to Comparative Preparation Example 1 and Comparative Preparation Example 2 instead of the copper complexes according to Preparation Example 1 to Preparation Example 4.

On the other hand, each wavelength vs. absorbance graph of the near-infrared absorbing compositions according to Examples 1 to 4 and Comparative Examples 1 and 2 is obtained by using a UV-Vis spectrophotometer (SoldiSpec-3700, Shimadzu Corp.).

Figure 6:
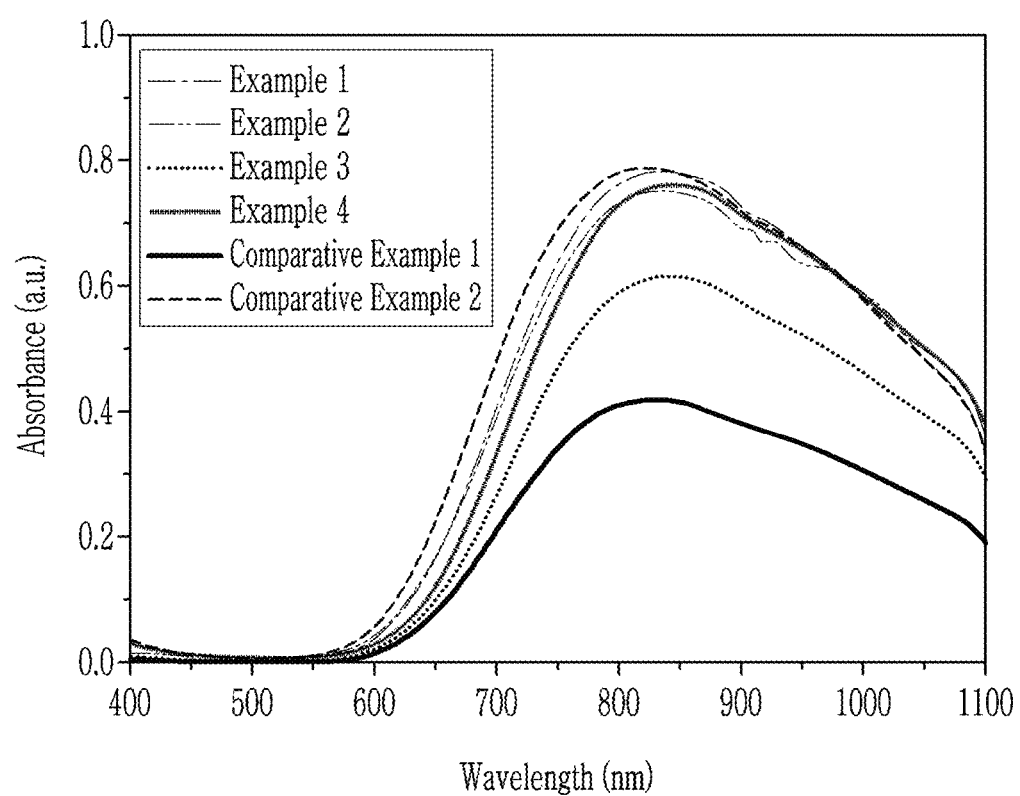
FIG. 6 is a graph showing absorbance vs. a wavelength of the near-infrared absorbing compositions according to Examples and Comparative Examples.

Herein, the wavelength vs. absorbance graphs of the near-infrared absorbing compositions according to Examples 1 to 4 and Comparative Examples 1 and 2 are shown in FIG. 6.

In addition, in FIG. 6, absorbance corresponding to a y-axis of each curve of Example 1 to Example 3 is normalized to have a maximum absorbance, and the normalized absorbance (An) is converted into light transmittance (T) to satisfy Equation 1. The results are shown in FIG. 7.

$$T = 10^{(2-An)} \quad \text{[Equation 1]}$$

In addition, regarding the near-infrared absorbing compositions according to Example 1 to Example 4 and Comparative Example 1 to Comparative Example 2, a maximum absorption wavelength ($\lambda_{NIR}$), maximum absorbance ($A_{NIR}$), average absorbance ($A_{430-565}$) in a visible light wavelength region (435 nm to 565 nm), an area of near-infrared wavelength region, and a cut-off wavelength ($\lambda_{cut-off}$) obtained from the wavelength vs. absorbance graph of FIG. 6 are summarized and shown in Table 1.

Figure 7:
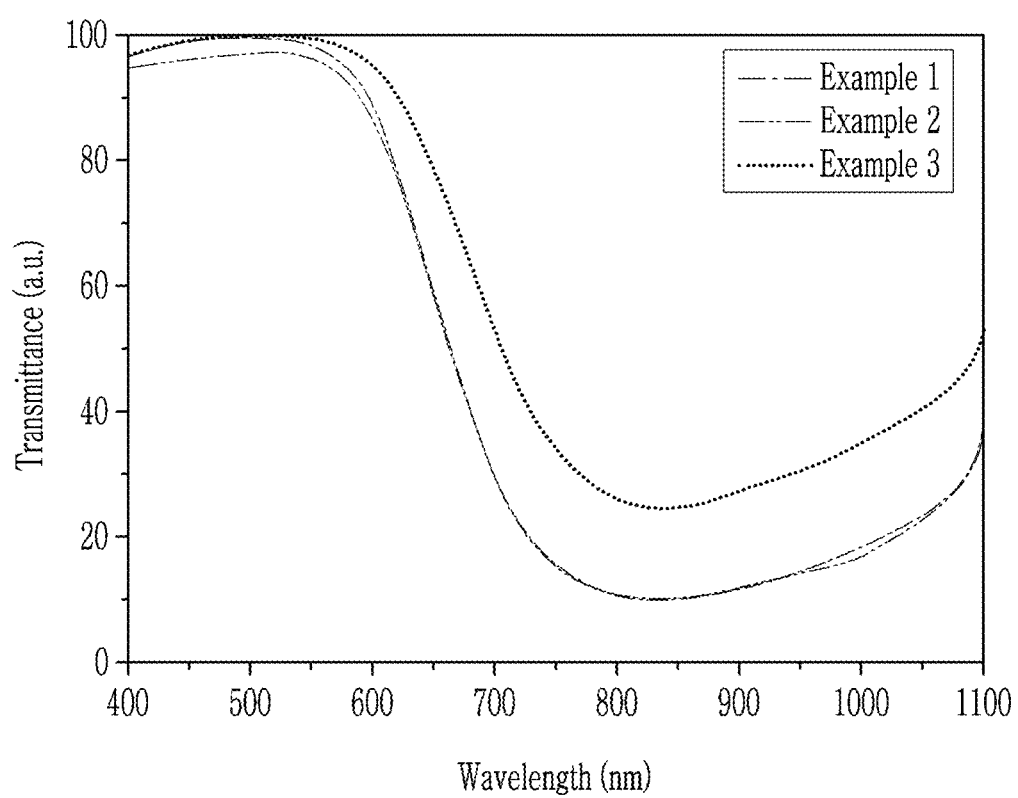
FIG. 7 is a graph showing light transmittance vs. a wavelength of the near-infrared absorbing compositions according to Examples.

In Table 1, $A_{NIR}$ is a measured value under the condition of a 10 mg/mL ethanol concentration, the area of the near-infrared wavelength region is an area obtained by integrating each curve of FIG. 6 in a wavelength range from 500 nm to 1100 nm, and the cut-off wavelength is a wavelength where light transmittance of each converted curve is 50% after converting a curve of wavelength vs. absorbance into a curve of wavelength vs. light transmittance in the same manner as FIG. 7.

TABLE 1

| | Copper complex | $\lambda_{NIR}$ [nm] | $A_{NIR}$ | $A_{430-565}$ | Area | $\lambda_{cut-off}$ [nm] |
|---|---|---|---|---|---|---|
| Example 1 | [Chemical Formula 1-1] | 834 | 0.78 | 0.005 | 274 | 665 |
| Example 2 | [Chemical Formula 1-2] | 834 | 0.75 | 0.012 | 267 | 664 |
| Example 3 | [Chemical Formula 1-3] | 840 | 0.61 | 0.004 | 210 | 677 |
| Example 4 | [Chemical Formula 1-8] | 834 | 0.76 | 0.010 | 262 | 676 |
| Comparative Example 1 | [Chemical Formula A] | 826 | 0.42 | 0.001 | 145 | 668 |
| Comparative Example 2 | [Chemical Formula B] | 814 | 0.78 | 0.008 | 284 | 652 |

Referring to FIGS. 6 and 7 and Table 1, the near-infrared absorbing compositions according to Examples satisfy maximum absorption wavelengths of greater than or equal to 830 nm and cut-off wavelengths of greater than or equal to 660 nm simultaneously and the maximum absorbance and areas of the near-infrared wavelength region are improved, which indicate improved near-infrared absorption capability. In addition, the near-infrared absorbing composition according to Examples may be a material having high visible ray transparency that shows average absorbance of less than or equal to 0.015 in a visible light wavelength region.

On the contrary, even if the cut-off wavelength of Comparative Example 1 is 668 nm, the maximum absorption wavelength is less than 830 nm, and the maximum absorbance and the areas of the near-infrared wavelength region may be largely deteriorated compared with Examples, which show unfavorable near-infrared absorption capability. The reason is that the copper complex of Comparative Example 1 has only homogeneous phosphate-based ligands unlike the copper complexes of Examples.

On the other hand, Comparative Example 2 has improved maximum absorbance and an increased area of the near-infrared wavelength region but shows a maximum absorption wavelength of 814 nm and a cut-off wavelength of 652 nm, which are respectively close to a short wavelength, compared with Examples. Accordingly, the near-infrared absorbing composition according to Comparative Example 2 provides a strong blue image (distorted color image) due to reduced visual information of a red wavelength region and thus may not be appropriate for an optical structure.

Accordingly, when a copper complex has at least two different ligands (an acetate-based ligand and a phosphate-based ligand), which do not shift a maximum absorption wavelength up to greater than or equal to about 830 nm unlike Examples, a desired result may not be obtained.

Manufacture of Near-Infrared Absorbing Film

Example 5 and Example 6

The near-infrared absorbing compositions according to Example 1 to Example 4 are bar-coated on a 100 μm-thick cycloolefin polymer (COP) film and photocured with a UV dose of about 500 mJ to form an optical structure including an about 100 μm-thick near-infrared absorption layer on the COP film. On the other hand, the thickness of the used COP film may be lowered to be about 40 μm within a range of 20 μm to 120 μm or releasing films may be removed in the subsequent process.

Comparative Example 3

An optical structure is manufactured according to the same method as Example 5 except for using the near-infrared absorbing composition prepared in Comparative Example 1 instead of the near-infrared absorbing composition prepared in Example 1.

Comparative Example 4

The copper complex prepared in Comparative Preparation Example 1 is formed into a film on about 100 μm-thick cycloolefin polymer (COP) film to manufacture an optical structure.

Comparative Example 5

An optical structure is manufactured according to the same method as Example 5 except for using the near-infrared absorbing composition prepared in Comparative Example 2 instead of the near-infrared absorbing composition prepared in Example 1.

Figure 8:
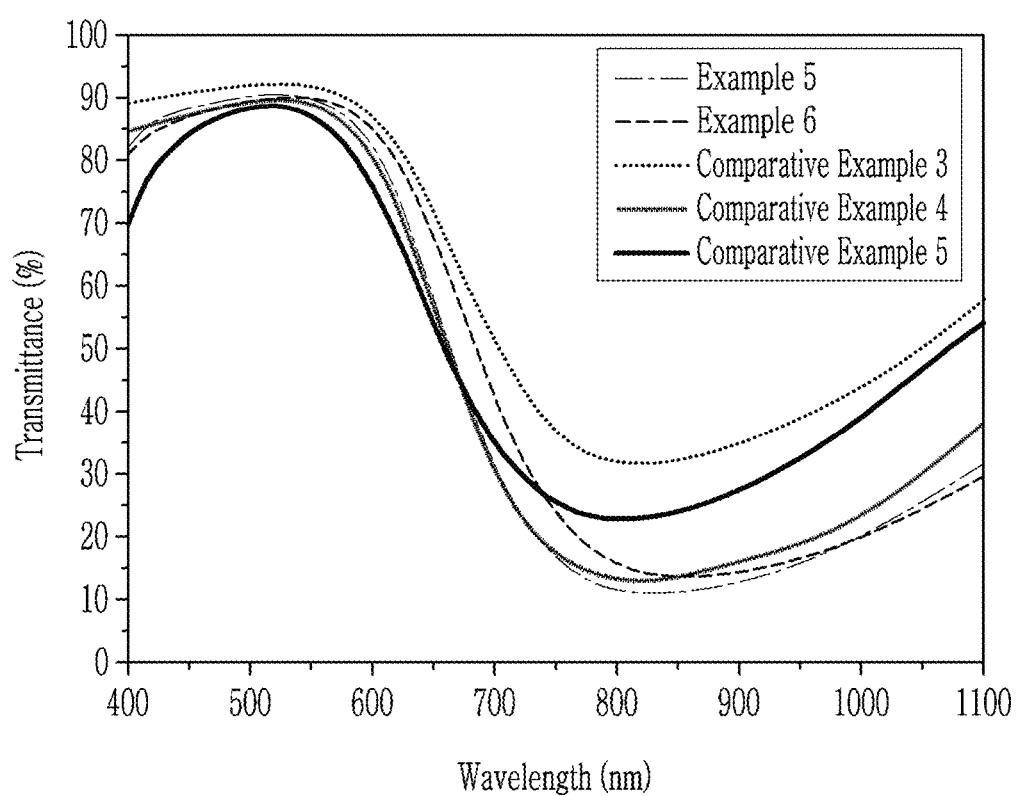
FIG. 8 is a graph showing light transmittance vs. a wavelength of the optical structures according to Example 5 to Example 6 and Comparative Example 3 to Comparative Example 5.

On the other hand, wavelength vs. light transmittance graphs of the optical structures according to Example 5, Example 6 and Comparative Example 3 to Comparative Example 5 are calculated by using a UV-Vis spectrophotometer (SoldiSpec-3700, Shimadzu Corp.) and shown in FIG. 8.

In addition, the amounts of the copper complexes in the near-infrared absorption layers of the optical structures according to Example 5, Example 6 and Comparative Example 3 to Comparative Example 5 and in addition, an average light transmittance at each wavelength region obtained from FIG. 8, a haze, a maximum absorption wavelength, and a cut-off wavelength are respectively shown in Table 2.

about 1200 nm compared with Examples and thus may not be appropriate for an optical structure.

The film of Comparative Example 4 is formed of 100% of a copper complex and shows a similar near-infrared blocking effect to those of Examples 5 and 6 but so low a cut-off wavelength as to be overlapped with that of a visible light wavelength region compared with those of Examples and accordingly, may cause a color distortion of a camera image. Therefore, the film of Comparative Example 4 may not be appropriate for an optical structure.

The film of Comparative Example 5 includes the copper complex represented by Chemical Formula B in a high amount (about 67 wt %) like those of Examples and thus has a crack, and accordingly, the amount of the copper complex may be limited to be 56 wt %. Accordingly, Comparative Example 5 shows high light transmittance of greater than or equal to 10% in a near-infrared entire wavelength region compared with Examples, so low a cut-off wavelength as to be overlapped with a visible light wavelength region compared with Examples and accordingly, may cause a color distortion of a camera image. Therefore, the film of Comparative Example 5 may not be appropriate for an optical structure.

While some example embodiments have been described, it is to be understood that the inventive concepts are not limited to the disclosed embodiments, but, on the contrary, cover various modifications and equivalent arrangements included within the spirit and scope of the appended claims.

TABLE 2

| | Amount of copper complex [wt %] | Average light transmittance [%] | | | | | | Haze [%] | $\lambda_{NIR}$ [nm] | Cut-off $\lambda_{cut-off}$ [nm] |
| | | 430 nm–565 nm | 700 nm–740 nm | 740 nm–850 nm | 850 nm–950 nm | 950 nm–1100 nm | 1100 nm–1200 nm | | | |
|---|---|---|---|---|---|---|---|---|---|---|
| Example 5 | 67 | 89.4 | 24.7 | 13.1 | 13.5 | 23.5 | 38.7 | 1.5 | 832 | 664 |
| Example 6 | 67 | 88.7 | 34.0 | 17.7 | 14.8 | 22.7 | 35.7 | 1.9 | 852 | 684 |
| Comparative Example 3 | 67 | 91.6 | 44.6 | 33.6 | 35.6 | 47.8 | 63.9 | 1.0 | 816 | 703 |
| Comparative Example 4 | 100 | 88.5 | 24.2 | 14.6 | 16.2 | 27.5 | 46.0 | 1.6 | 816 | 660 |
| Comparative Example 5 | 56 | 86.7 | 30.5 | 24.1 | 28.1 | 43.3 | 60.6 | 1.6 | 821 | 658 |

Referring to FIG. 8 and Table 2, the optical structures using the heterogeneous ligand copper complexes according to Examples show excellent visible light transmittances and near-infrared blocking effects compared with Comparative Examples.

On the other hand, Example 6 without the polymerizable monomer shows a little increased haze compared with Example 5 and may further need an additive for fixing the copper complex. However, Example 6 shows an improved cut-off wavelength compared with Example 5 and improved visible light transmittance and near-infrared blocking effects.

On the other hand, Comparative Example 3 shows remarkably increased light transmittance in an entire wavelength region of a near-infrared ray ranging from 700 nm to <Description of Symbols>

10: near-infrared absorbing film
11: transparent substrate
12: near-infrared absorption layer
13, 14: infrared reflection layer -continued <Description of Symbols>

20: camera module
21: lens barrel
22: housing
23: image sensor
23A: organic CMOS image sensor
50a, 50b: photo-sensing device
70: color filter layer
60, 80: insulation layer
200: organic photoelectric device
210: lower electrode
220: upper electrode
230: absorption layer

What is claimed is:

1. A near-infrared absorbing composition comprising:
a copper complex represented by Chemical Formula 1,

[Chemical Formula 1]

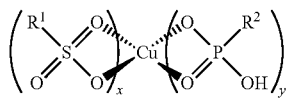

wherein, in Chemical Formula 1, $R^1$ and $R^2$ are independently one of hydrogen, deuterium, a substituted or unsubstituted C1 to C20 alkyl group, a substituted or unsubstituted C1 to C20 alkenyl group, a substituted or unsubstituted C1 to C20 alkynyl group, a substituted or unsubstituted C1 to C20 cycloalkyl group, a substituted or unsubstituted C1 to C20 aryl group, a substituted or unsubstituted C1 to C20 heteroaryl group, a photo-polymerizable functional group, $-OR^{a1}$, $-C(=O)R^{a2}$, or $-OC(=O)R^{a3}$ wherein $R^{a1}$, $R^{a2}$, and $R^{a3}$ are independently one of hydrogen, deuterium, a substituted or unsubstituted C1 to C20 alkyl group, a substituted or unsubstituted C1 to C20 alkenyl group, a substituted or unsubstituted C1 to C20 cycloalkyl group, a substituted or unsubstituted C1 to C20 aryl group, or a substituted or unsubstituted C1 to C20 heteroaryl group, $0 < x \leq 4$, and $0 < y \leq 4$.

2. The near-infrared absorbing composition of claim 1, wherein the photo-polymerizable functional group comprises a functional group represented by Chemical Formula 11,

[Chemical Formula 11]

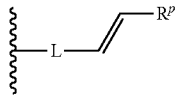

wherein, in Chemical Formula 11,

L is one of a single bond, a substituted or unsubstituted C1 to C20 alkylene group, a substituted or unsubstituted C1 to C20 cycloalkylene group, a substituted or unsubstituted C1 to C20 arylene group, a substituted or unsubstituted C1 to C20 heteroarylene group, $-O-$, $-S-$, $-C(=O)-$, or a combination thereof, and $R^p$ is one of hydrogen, deuterium, a substituted or unsubstituted C1 to C20 alkyl group, a substituted or unsubstituted C1 to C20 aryl group, or a substituted or unsubstituted C1 to C20 heteroaryl group.

3. The near-infrared absorbing composition of claim 1, wherein at least one of $R^1$ and $R^2$ is a photo-polymerizable functional group.

4. The near-infrared absorbing composition of claim 3, wherein $R^1$ is one of a substituted or unsubstituted C1 to C20 alkyl group, a substituted or unsubstituted C1 to C20 cycloalkyl group, or a substituted or unsubstituted C1 to C20 aryl group, and $R^2$ is a photo-polymerizable functional group.

5. The near-infrared absorbing composition of claim 1, wherein the copper complex is represented by Chemical Formula 2:

[Chemical Formula 2]

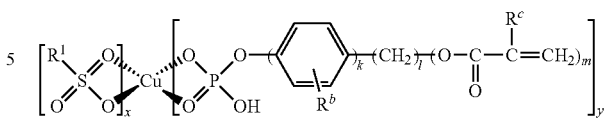

wherein, in Chemical Formula 2, $R^1$, x, and y are the same as defined in claim 1, respectively, $R^b$ and $R^c$ are independently one of hydrogen, deuterium, a substituted or unsubstituted C1 to C20 alkyl group, a substituted or unsubstituted C1 to C20 cycloalkyl group, a substituted or unsubstituted C1 to C20 aryl group, or a substituted or unsubstituted C1 to C20 heteroaryl group, k and l are independently an integer ranging from 0 to 8, and m is 0 or 1.

6. The near-infrared absorbing composition of claim 5, wherein m is 1 and one of k and l is 0.

7. The near-infrared absorbing composition of claim 5, wherein m is 1, and k and l are independently be an integer in a range of 1 to 8.

8. The near-infrared absorbing composition of claim 1, wherein the near-infrared absorbing composition includes one or more compounds represented by Chemical Formula 1-1 to Chemical Formula 1-8:

[Chemical Formula 1-1]

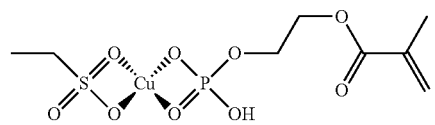

[Chemical Formula 1-2]

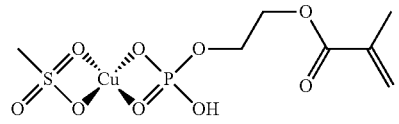

[Chemical Formula 1-3]

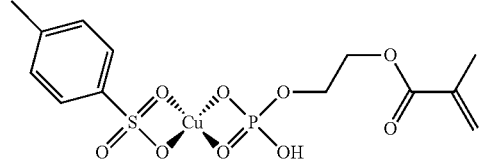

[Chemical Formula 1-4]

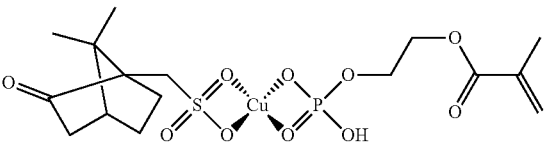

[Chemical Formula 1-5]

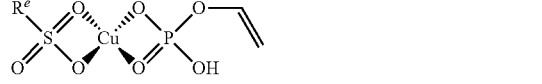

[Chemical Formula 1-6]

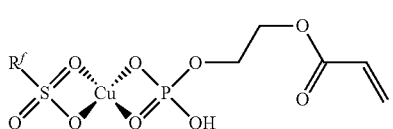

[Chemical Formula 1-7]

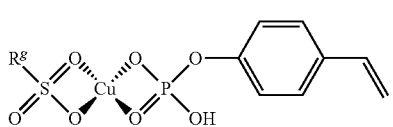

[Chemical Formula 1-8]

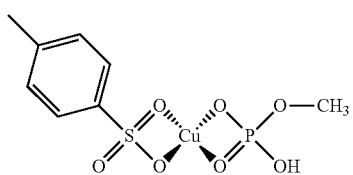

wherein, in Chemical Formula 1-1 to Chemical Formula 1-8, $R^e$, $R^f$, and $R^g$ are independently one of hydrogen, deuterium, a substituted or unsubstituted C1 to C20 alkyl group, a substituted or unsubstituted C1 to C20 cycloalkyl group, or a substituted or unsubstituted C1 to C20 aryl group.

9. The near-infrared absorbing composition of claim 1, further comprising: a polymerizable monomer that is thermally cross-linkable or photo-cross-linkable; and
a solvent.

10. The near-infrared absorbing composition of claim 9, wherein the polymerizable monomer includes an acryl-based monomer, an epoxy-based monomer, a vinyl-based monomer, or a combination thereof.

11. The near-infrared absorbing composition of claim 9, wherein the solvent includes ethanol, methanol, benzene, toluene, xylene, NMP (N-methylpyrrolidone), acrylonitrile, acetonitrile, THF (tetrahydrofuran), ethyl acetate, MEK (methylethylketone), butylcarbitol, butylcarbitolacetate, butylcellosolve, butylcellosolveacetate, ethylcarbitol, ethylcarbitolacetate, IPA (isopropylalcohol), acetone, DMF (dimethyl formamide), DMSO (dimethylsulfoxide), piperidine, phenol, MIBK (methylisobutylketone), PGME (1-methoxy-2-propanol), PGMEA (propylene glycolmonomethyl ether acetate), or a combination thereof.

12. The near-infrared absorbing composition of claim 1, wherein the near-infrared absorbing composition has a maximum absorption wavelength of about 830 nm to about 900 nm.

13. The near-infrared absorbing composition of claim 1, wherein the near-infrared absorbing composition has a cut-off wavelength of about 660 nm to about 700 nm.

14. An optical structure comprising:
a near-infrared absorption layer formed using the near-infrared absorbing composition of claim 1.

15. The optical structure of claim 14, wherein the copper complex is included in an amount of about 50 wt % to about 100 wt % based on a total weight of the near-infrared absorption layer.

16. The optical structure of claim 14, wherein the near-infrared absorption layer further includes an acryl-based polymer, an epoxy-based polymer, or a combination thereof.

17. The optical structure of claim 14, wherein the optical structure has an average light transmittance of greater than or equal to about 80% in a wavelength region of about 430 nm to about 565 nm, when measured at a thickness of about 120 μm to about 220 μm.

18. The optical structure of claim 14, wherein the optical structure has an average light transmittance of less than or equal to about 15% in a wavelength region of about 740 nm to about 950 nm, when measured at a thickness of about 120 μm to about 220 μm.

19. The optical structure of claim 14, wherein the optical structure has an average light transmittance of less than or equal to about 25% in a wavelength region of about 700 nm to about 740 nm, when measured at a thickness of about 120 μm to about 220 μm.

20. The optical structure of claim 14, wherein the optical structure has a haze of greater than 0% and less than or equal to about 3% in a wavelength region of about 435 nm to about 565 nm, when measured at a thickness of about 120 μm to about 220 μm.

21. A camera module comprising
a lens;
an image sensor; and
the optical structure of claim 14 between the lens and the image sensor.

22. An electronic device comprising:
the optical structure of claim 14.

* * * * *